(12) United States Patent
Ammann

(10) Patent No.: US 7,553,318 B2
(45) Date of Patent: Jun. 30, 2009

(54) DEVICE FOR PRODUCING A FLUID JET USED ESPECIALLY TO REMOVE BIOLOGICAL TISSUE, AND USE THEREOF

(75) Inventor: Roger Ammann, Erlinsbach (CH)

(73) Assignee: Medaxis AG, Aarau (CH)

( * ) Notice: Subject to any disclaimer, the term of this patent is extended or adjusted under 35 U.S.C. 154(b) by 844 days.

(21) Appl. No.: 10/311,754

(22) PCT Filed: Jun. 19, 2001

(86) PCT No.: PCT/CH01/00385

§ 371 (c)(1),
(2), (4) Date: Dec. 19, 2002

(87) PCT Pub. No.: WO01/97700

PCT Pub. Date: Dec. 27, 2001

(65) Prior Publication Data

US 2008/0172075 A1  Jul. 17, 2008

(30) Foreign Application Priority Data

Jun. 20, 2000 (CH) .................................. 1213/00

(51) Int. Cl.
*A61B 17/32* (2006.01)

(52) U.S. Cl. .................... 606/167; 606/131; 604/19

(58) Field of Classification Search ................. 606/131, 606/167; 604/43, 22, 27, 141, 143
See application file for complete search history.

(56) References Cited

U.S. PATENT DOCUMENTS

| | | | | |
|---|---|---|---|---|
| 4,913,698 A | * | 4/1990 | Ito et al. | 604/22 |
| 5,524,821 A | * | 6/1996 | Yie et al. | 239/10 |
| 5,591,184 A | * | 1/1997 | McDonnell et al. | 606/167 |
| 5,853,384 A | * | 12/1998 | Bair | 604/22 |
| 5,871,462 A | * | 2/1999 | Yoder et al. | 604/22 |
| 6,224,378 B1 | * | 5/2001 | Valdes et al. | 433/224 |

* cited by examiner

*Primary Examiner*—Nicholas D Lucchesi
*Assistant Examiner*—Christopher D Koharski
(74) *Attorney, Agent, or Firm*—Wenderoth, Lind & Ponack, L.L.P.

(57) ABSTRACT

The invention relates to a fluid jet device for producing a liquid used to remove, in particular, biological tissue. The fluid jet device comprises housing in which a pump set is arranged for producing high liquid pressure within a range of up to 800 bars. A pressure supplying source and the nozzle which produces the liquid jet can be connected to the pump set, the nozzle being connected by a flexible connecting line. The hole diameter of the nozzle outlet measures between 20 to 120 micrometers. The weight of the housing with the pump set and the separate pressure supplying source for the pump set respectively is such that they are especially suitable for mobile use and can therefore respectively be carried by hand.

19 Claims, 1 Drawing Sheet

DEVICE FOR PRODUCING A FLUID JET USED ESPECIALLY TO REMOVE BIOLOGICAL TISSUE, AND USE THEREOF

BACKGROUND OF THE INVENTION

This invention concerns a fluid jet device for producing a liquid jet especially to remove biological tissue, with an appliance in which a pump set is arranged for producing high liquid pressure within a range of up to 800 bars. A pressure supplying source can be connected to the fluid jet device for producing the liquid jet, and also connected to a nozzle which produces the liquid jet by a flexible connecting line. The discharge orifice of the nozzle is between 20 and 120 micrometers in diameter.

The generic type surgical device according to specification EP-A-0 232 678 has a pump set which generates pressure and is connected by a flexible metal line to a nozzle for delivering a liquid jet, and the initial speed of the jet is equal to or greater than the mach number. This pump set as well as the other accessories are normally arranged and mounted within a housing. Since such a liquid jet cutting device is used especially in surgery, as for example in liver operations for destroying liver parenchymas or the like, the design of this device, together with the pressure supply system designed as a compressor for the pump set, is appropriately solid and heavy.

However, the purpose of this invention is to create a device within the generic concept described at the beginning, but which is also particularly suitable, in its portable version carried by operators, for ambulatory treatment of patients. It must also be possible to use this device for new treatment applications not only administered by doctors and medics but also carers, paramedics and the like.

SUMMARY OF THE INVENTION

The invention achieves this purpose by the fact that the weight of the fluid jet device and the separate pressure supply source provided for the pump set is such that they are particularly suitable for use in portable applications and can accordingly be carried by hand.

This device according to the invention can be used for ambulatory treatment of patients practically independent of the locations where such treatment could not be performed with the use of existing equipment.

In addition, the purpose is also achieve in accordance with the invention thanks to the fact that this liquid jet can be used for cleaning wounds or treating wounds such as burns, abscesses, sores or the like.

The portable design of this device can thus be used for treating patients outside operating rooms, including those who are not hospitalized.

It has become surprisingly apparent that wounds treated by the fluid jet heal faster than those treated by conventional means.

BRIEF DESCRIPTION OF THE DRAWINGS

An embodiment of the invention and its further advantages are described in greater detail with reference to the drawing, in which.

DETAILED DESCRIPTION OF THE INVENTION

Figure 1:
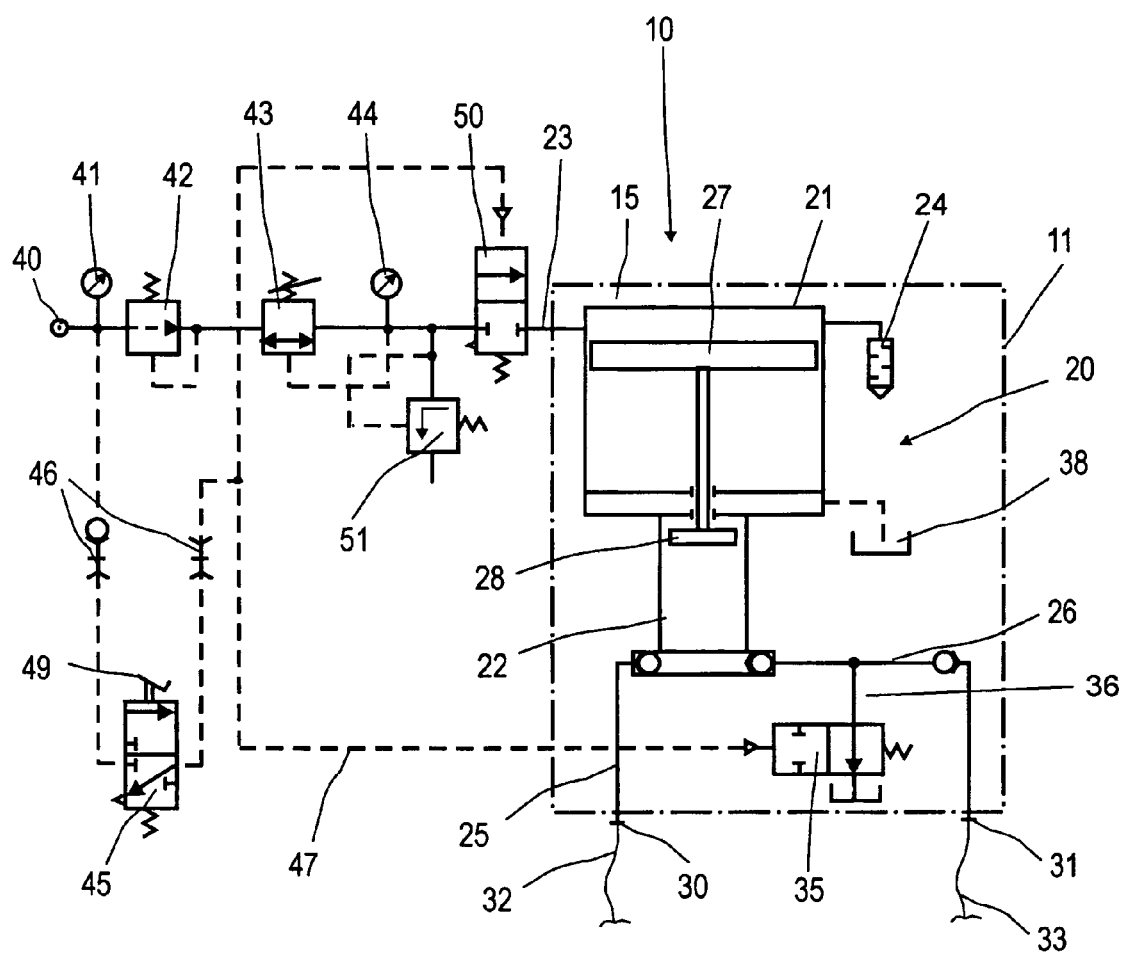
FIG. 1 is a block diagram of a device in accordance with the invention.

FIG. 1 shows a block diagram of a fluid jet device 10 for producing a fluid jet to be used especially to remove biological tissue. This fluid jet device 10 can be used to great advantage for cutting away parts of tissue, especially parenchymal tissue, for example in liver, kidney and similar operations.

The device 10 has a housing 11 which contains a pump set 20 for generating a high pressure of the cutting fluid up to 800 bar. This pump set 20 is preferably designed as a conventional differential piston pump supplied with compressed air from a pressure supply source such as a compressed air main or a separate compressed air generating device. The pump 20 includes a first larger cylinder 21 in the form of a low pressure section with a large drive piston 27 reciprocating within it, and a second smaller high pressure cylinder 22 arranged coaxially in relation to the first cylinder. The second cylinder 22 includes smaller plunger piston 28 connected to the drive piston 27. The first larger cylinder 21 is connected to an air feed line 23 and an outlet valve 24 for compressed air while the high pressure cylinder 22 is connected to a feed line 25 and an outlet line 26 for the fluid. The feed line 25 and the outlet line 26 each lead to a connection plug 30, 31 accessible outside the housing 11. The first plug (fluid inlet) 30 is connectable to a hose 32 connected to a fluid tank (fluid source), and the second plug (fluid outlet) 31 is connectable to a flexible metal hose 33. The fluid tank contains a physiological solution, for example a sterile common salt solution with approx. 0.9% of common salt or similar component. A nozzle provided with a handle for manual operation of this cutting equipment, producing the fluid jet, is attached at the end of this flexible metal hose 33.

According to the invention, the total weight of the housing 11 with the pump 20 and the pressure supply source for the pump 20 separately connectable to the pump set 20 is such that they are suitable especially for portable use and can each be carried by hand. The pressure supply source 40 can operate independently of a main line or a gas pressure main line.

Furthermore, it is precisely due to the portable design of this device that a wound can be cleaned or treated with this fluid jet very economically in the case of burns, abscesses, sores or the like.

Moreover, a pressure relief valve 35, connected via a connecting line 36 to the outlet line 26 of the pump, is attached at the high-pressure outlet of the pump set 20.

The whole pump set 20 is advantageously mounted on a bearing element 15 within the housing 11 indicated by a dash dot line. This pump set 20 includes the differential piston pump with cylinders 21, 22 and the pistons 27, 28 arranged within them, the high-pressure side feed line 25 and outline 26 as the lines connecting to the connection plugs 30, 31, and the air-operated pressure relief valve 35. The compressed air inlet (feed) line 23 and the outlet valve 24 are also arranged at the cylinder 21.

Compressed air is carried from a pressure supply source 40, a pressure gauge 41, a safety pressure reduction valve 42, a regulating valve 43, an operating pressure gauge 44, and a control valve 50 through the air feed line (pressure supply line) 23 to the inlet at the LP cylinder 21.

The pressure supply source 40 can be a gas bottle containing gas under a pressure of between 4 and 10 bars, feeding gas to the low pressure cylinder 21. The gas cylinder is advantageously in the form of a plastic bottle which can be easily carried by hand.

The pressure supply source 40 and pump set 20 are switched off or into operation to produce the water jet by a conventional pedal 49. This pedal 49, which is provided with couplings 46 connected to the control line 47, operates a two-way valve 45 which causes, in the closed state shown, the control valve 50 to be closed with the pressure relief valve 35 reducing the water pressure and, thus, with no water jet flowing. On the other hand, with the foot pedal 49 pressed down and thus the valve 45 open, control valve 50 is open and pressure relief valve 35 closed. This causes the pump set to be switched on and water to be delivered to the nozzle. On releasing the pedal 49, control valve 50 closes automatically and switches the fluid jet device automatically to its pressureless state.

The nozzle with the handle for the actual operating action to produce the water jet (not shown here in detail) is made of high-quality metal no matter whether it is used for cutting out tissue or for the treatment of wounds. This offers a further advantage within the framework of the invention due to the fact that this nozzle can be used many times. Thus, the maintenance costs are lower than in the case of one-off use. Furthermore, the diameter of the nozzle outlet is between 20 and 120 micrometers.

The invention is sufficiently explained on the basis of the above embodiments. Nevertheless, it can be made in other versions. For example, the pump set can be designed differently than presented here. In principle, an electrically operated pump could also be used as the pressure supply source.

The invention claimed is:

1. A fluid jet device for producing a fluid jet, comprising:
   a housing;
   a pump set arranged in said housing, said pump set including a differential piston pump operable to produce a high liquid pressure for removing biological tissue;
   a pressure supplying source separate from said pump set, and operable to be connected to said differential piston pump of said pump set via a pressure supply line;
   a nozzle connectable by a flexible connecting line to a high-pressure fluid outlet of said differential piston pump for emitting the fluid jet, said nozzle having a nozzle outlet with a diameter of between 20 micrometers and 120 micrometers; and
   a pump control system including:
      a control valve in said pressure supply line;
      a pressure relief valve at said high-pressure fluid outlet of said differential piston pump, wherein said control valve and said pressure relief valve of said pump control system are operable in unison to control an operation of said differential piston pump; and
      a two-way valve having an inlet line connected to said pressure supply line upstream of said control valve, said two-way valve further having an outlet line connected to said control valve and said pressure relief valve.

2. The fluid jet device of claim 1, wherein said pressure supplying source is operable independently of either an electrical main line or a gas pressure main line.

3. The fluid jet device of claim 2, wherein said pressure supplying source comprises a compressed air supply source, said differential piston pump comprising a low pressure section to be connected to said compressed air supply source and a high pressure section having a first plug to be connected to a fluid source and a second plug to be connected to said nozzle.

4. The fluid jet device of claim 2, wherein said nozzle has a handle, and said nozzle and handle are made of a metal to allow reuse.

5. The fluid jet device of claim 2, wherein said pressure supplying source comprises a compressed gas bottle containing gas at a pressure between 4 and 10 bar.

6. The fluid jet device of claim 5, wherein said differential piston pump comprises a low pressure section to be connected to said compressed gas bottle and a high pressure section having a first plug to be connected to a fluid source and a second plug to be connected to said nozzle.

7. The fluid jet device of claim 5, wherein said nozzle has a handle, and said nozzle and handle are made of a metal to allow reuse.

8. The fluid jet device of claim 2, wherein said pressure supplying source comprises a plastic compressed gas bottle.

9. The fluid jet device of claim 8, wherein said differential piston pump comprises a low pressure section to be connected to said plastic compressed gas bottle and a high pressure section having a first plug to be connected to a fluid source and a second plug to be connected to said nozzle.

10. The fluid jet device of claim 8, wherein said nozzle has a handle, and said nozzle and handle are made of a metal to allow reuse.

11. The fluid jet device of claim 1, wherein said pressure supplying source comprises a compressed air supply source, said differential piston pump comprising a low pressure section to be connected to said compressed air supply source and a high pressure section having a first plug to be connected to a fluid source and a second plug to be connected to said nozzle.

12. The fluid jet device of claim 11, wherein said nozzle has a handle, and said nozzle and handle are made of a metal to allow reuse.

13. The fluid jet device of claim 1, wherein said nozzle has a handle, and said nozzle and handle are made of a metal to allow reuse.

14. The fluid jet device of claim 1, wherein said pressure supplying source comprises a compressed gas supply source, said differential piston pump comprising:
   a low pressure cylinder to be connected to said compressed gas supply source;
   a drive piston arranged in said low pressure cylinder so as to be driven by compressed gas supplied into said large low pressure cylinder;
   a high pressure section having a fluid inlet to be connected to a fluid source and having a fluid outlet to be connected to said nozzle; and
   a plunger piston connected to said drive piston so as to be driven by said drive piston.

15. The fluid jet device of claim 1, wherein said pump control system further includes a pedal operator for opening and closing said two-way valve, said pump control system being arranged such that, when said two-way valve is closed by said pedal operator, said control valve is closed and said pressure relief valve is opened so as to reduce a pressure output from said differential piston pump, and such that, when said two-way valve is opened by said pedal operator, said control valve is opened and said pressure relief valve is closed so as to increase the pressure output from said differential piston pump.

16. The fluid jet device of claim 1, wherein said differential piston pump is operable to generate a high liquid pressure of 800 bar.

17. A method of producing a fluid jet using a pump set arranged in a housing, the pump set including a differential piston pump operable to produce a high liquid pressure, said method comprising:

connecting a pressure supplying source separate from the pump set to the differential piston pump of the pump set via a pressure supply line;

connecting a nozzle to a high-pressure fluid outlet of the differential piston pump by a flexible connecting line, the nozzle having a nozzle outlet with a diameter of between 20 micrometers and 120 micrometers for emitting the fluid jet;

connecting a fluid source to the differential piston pump; and applying pressure to the differential piston pump via the pressure supplying source so as to operate the differential piston pump and cause the fluid jet to emit from the nozzle; and controlling an operation of the differential piston pump by operating in unison a control valve in the pressure supply line and a pressure relief valve at the high-pressure fluid outlet of the differential piston pump, said controlling of the operation of the differential piston pump comprising:

connecting an inlet line of a two-way valve to the pressure supply line upstream of the control valve, and connecting an outlet line of the two-way valve to the control valve and the pressure relief valve;

closing the two-way valve using a pedal operator to close the control valve and open the pressure relief valve so as to reduce a pressure output from the differential piston pump; and opening the two-way valve using the pedal operator to open the control valve and close the pressure relief valve so as to increase the pressure output from the differential piston pump.

18. The method of claim 17, wherein a weight of each of the pump set arranged in the housing and the pressure supplying source is such that each is portable and can thus be carried by hand.

19. The method of claim 17, wherein said controlling of the differential piston pump generates a high liquid pressure of 800 bar.

* * * * *